United States Patent [19]
Boebel et al.

[11] Patent Number: 6,102,910
[45] Date of Patent: Aug. 15, 2000

[54] MEDICAL INSTRUMENT

[75] Inventors: Manfred Boebel, Oetisheim; Dieter Metsch, Kraichtal-Bahnbruecken, both of Germany

[73] Assignee: Richard Wolf GmbH, Knittlingen, Germany

[21] Appl. No.: 09/146,801

[22] Filed: Sep. 3, 1998

[30] Foreign Application Priority Data

Oct. 28, 1997 [DE] Germany .............................. 197 47 528

[51] Int. Cl.⁷ .................................................. A61B 17/36
[52] U.S. Cl. ............................................. 606/52; 606/205
[58] Field of Search .................................. 606/1, 32, 45,
606/40, 49, 37, 167, 174, 205–211, 190–200,
50, 51, 52; 600/201, 204, 210

[56] References Cited

U.S. PATENT DOCUMENTS

| | | | |
|---|---|---|---|
| 4,607,620 | 8/1986 | Storz | 606/206 |
| 5,147,378 | 9/1992 | Markham | 606/206 |
| 5,273,524 | 12/1993 | Fox et al. | |
| 5,454,378 | 10/1995 | Palmer et al. | |
| 5,514,089 | 5/1996 | Walbrink | |

FOREIGN PATENT DOCUMENTS

| | | |
|---|---|---|
| 25 19 827 B2 | 6/1977 | Germany . |
| 25 19 827 C3 | 2/1978 | Germany . |
| 41 19 592 A1 | 12/1992 | Germany . |
| 43 41 061 C1 | 12/1993 | Germany . |
| 43 23 584 A1 | 1/1995 | Germany . |

*Primary Examiner*—Glenn K. Dawson
*Attorney, Agent, or Firm*—Akin, Gump, Strauss, Hauer & Feld, L.L.P.

[57] ABSTRACT

A medical instrument having an inner part which is releasably fastened in the instrument on a proximal end and at the distal end carries a tool which can be actuated by way of an actuation element which is adjustable axially and relative to the inner part and the tool. The actuation element is releasably lockable in a proximal-side, axially adjustable receiver which drives the actuation element at the same time.

12 Claims, 2 Drawing Sheets

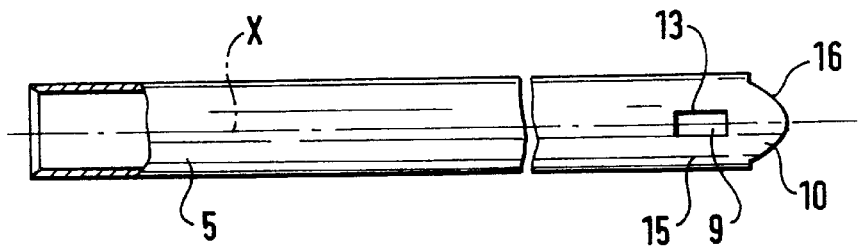
FIG. 2A
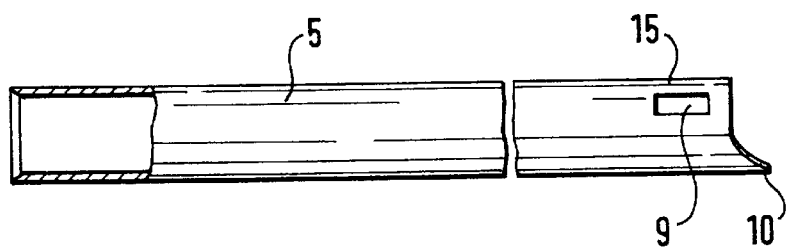
FIG. 2B
FIG. 3A
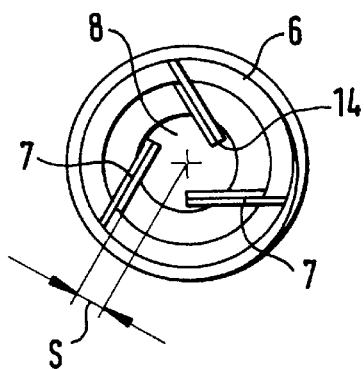
FIG. 3B
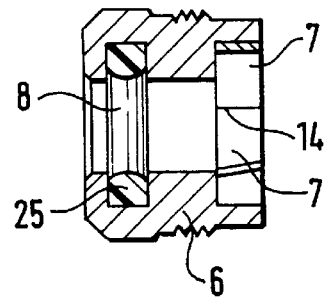
FIG. 4A
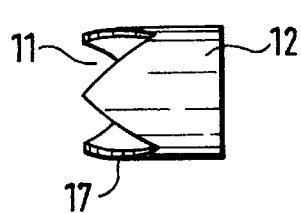
FIG. 4B
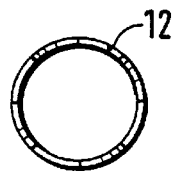

MEDICAL INSTRUMENT

BACKGROUND OF THE INVENTION

This invention relates to a medical instrument with an inner part which is releasably fastened in the instrument on the proximal side and which at the distal end carries a tool which can be actuated by way of an actuation element adjustable axially and relative to the inner part and the tool.

Such an instrument is described in the patent DE 25 19 827. With this instrument forming a HF coagulation forceps, with an actuation element guided in an outer shank, a forceps jaw provided on the instrument at the distal side is actuated. The end of the forceps insert on the proximal side is releasably connected to one arm of a handle by way of a coupling formed in a design manner as a blocking slide. The actuation element is releasably connected via an olive handle to the outer arm of the handle actuating it.

BRIEF SUMMARY OF THE INVENTION

It is the object of the invention to provide a medical instrument of the known type with simple mechanics which have the effect that an instrument insert introduced into an instrument shank on the one hand automatically aligns in its position to the outer shank and on the other hand without additional mechanical locking having to be carried out, on reaching a predetermined position within the outer shank, is automatically fixed and that the instrument insert can be easily unlocked and withdrawn from the instrument shank.

A medical instrument according to the invention achieving the above object is characterised in that the actuation element adjusting the tool by way of axial displacement is releasably lockable in a proximal-side, axially adjustable receiver which drives the actuation element at the same time. By way of the design of the instrument according to the invention on the one hand an instrument insert can be automatically releasably fixed in a predetermined position and on the other hand the instrument insert may be removed in a simple way and manner without additional auxiliary means.

In one embodiment form of the invention the actuation element is tubular and surrounds the inner part. For the simple locking and unlocking the tubular actuation element at its proximal end lying within the tubular receiver comprises at least one recess, and the receiver accommodating the actuation element has at least one spring element which is displaced about a certain predetermined distance with respect to the instrument longitudinal axis and in the locked position engages resiliently into the recess at the proximal end of the receiver.

With the unlocking the spring element cooperates with the mentioned recess at the proximal end of the actuation element in a manner such that the latter is only rotatable in the receiver in a certain rotational direction, e.g. in the clockwise direction, and with this rotation the spring element is removed from engagement with the recess.

With a particularly advantageous embodiment form the proximal end of the actuation element is provided with three recesses displaced in the circumferential direction about 120°. The receiver then likewise comprises three spring elements corresponding to these recesses arranged displaced by 120° to one another.

A guiding lug which is further provided at the proximal end of the tubular actuation element, in the form of a wall section projecting in the axial direction and tapering proximally, engages into a corresponding V-shaped, end-face recess of a cylindrical positioning element connecting proximally axially onto the actuation element. It is particularly advantageous when the positioning element on the end face comprises three V-shaped recesses displaced about 120° to one another. In this manner with the unlocking rotation of the actuation element a lateral edge of the guiding lug may slide along the edge of the positioning element, this edge corresponding to the lateral edge, being arranged obliquely to the instrument axis and limiting the V-shaped recess, by which means the actuation element additionally with the rotation is displaced distally and by way of this can be pulled more easily from the receiver.

BRIEF DESCRIPTION OF THE DRAWINGS

The invention is hereinafter described by way of an embodiment example shown in the drawing. There are shown.

DETAILED DESCRIPTION OF THE INVENTION

Figure 1:
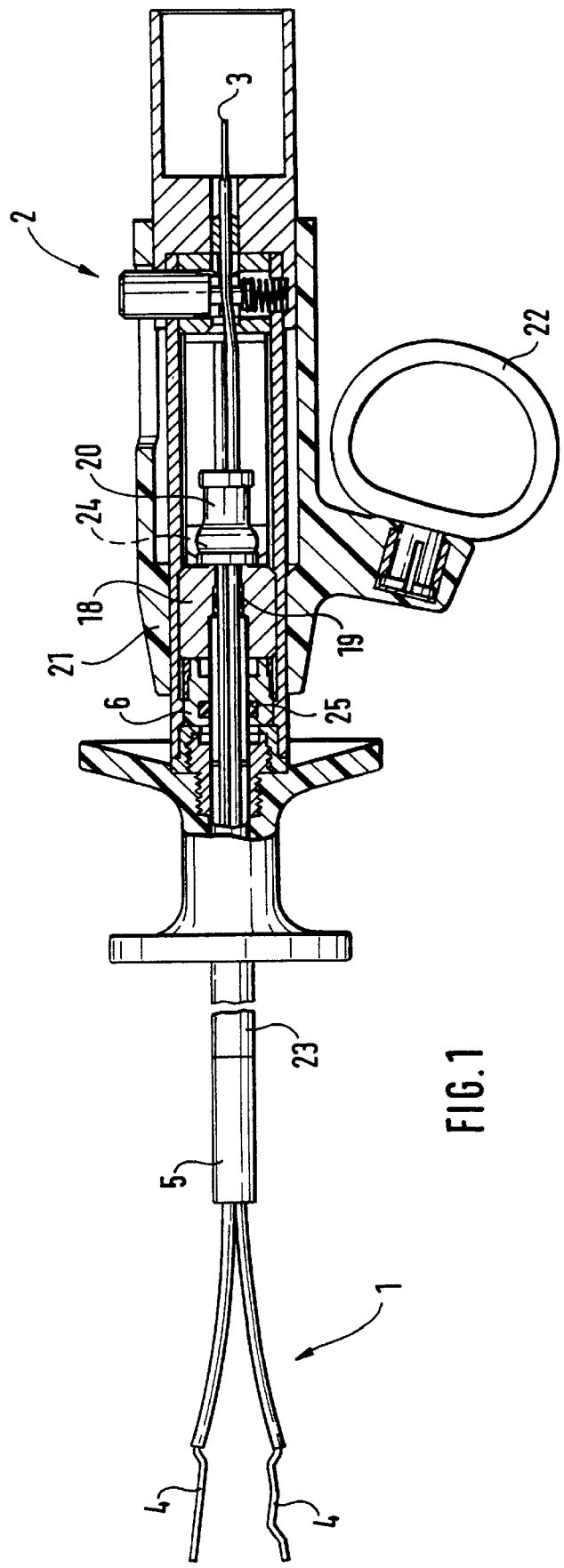
FIG. 1: a schematic, partly sectioned lateral view of a medical instrument according to a preferred embodiment form of the invention, FIGS. 2A/B: schematically the proximal end of the tubular actuation element in each case in a plan view and a lateral view, FIGS. 3A/B: schematically the annular receiver accommodating the actuation element according to FIG. 2 in each case in a plain view from the proximal side and in longitudinal section and FIGS. 4A/B: the positioning element which engages on the guiding lug at the proximal end of the actuation element, in each case in a lateral view and in a view on the distally directed end face.

The instrument according to FIG. 1 comprises a shank inner part 1 in the form of a forceps insert. This type of tool is however only an example since also other tools, for example inserts with coagulation clamps, grippers, scissors, cutters etc may be applied. The inner part 1 runs through the complete instrument and ends at its proximal end as a high frequency connection 3 to which for electro-surgery a suitable high frequency voltage may be applied. The inner part 1 is releasably and rotationally securely fixed by a blocking slide 2 which engages at its proximal end and is known per se.

For actuation, i.e. for closing and opening the forceps jaw 4 shown in FIG. 1, the inner part 1 is surrounded by a tubular actuation element 5 which with hand actuation of a thumb ring 22 formed on the lower side of the instrument may be displaced axially in the direction of the forceps jaw 4 or may be proximally retracted.

According to the invention this actuation element 5 may also be removed in order be able to ensure the hygenic requirements which are demanded of such types of medical instruments in the context of a perfect disinfection of all instrument parts. For this at the proximal end of the actuation element lying within a tubular receiver there are formed three recesses, and the annular receiver 6 likewise comprises spring elements which are displaced about a certain distance s with respect to the instrument longitudinal axis x and in the locking position resiliently engage into the recesses 9 (cf. FIG. 3A). The three spring elements 7 and also the three recesses 9 are each angularly displaced by 120° to one another in the circumferential direction and have a certain play to one another in the instrument longitudinal axis. It is to be noted that the number of recesses is directed to the number of spring elements 7 arranged in the receiver 6, but basically may be freely selected.

In the locked position the spring elements 7 engage into the recesses 9. Furthermore the actuation element 5 comprises at its proximal end a guiding lug 10 which projects in the axial direction and which tapers proximally. This guiding lug 10 engages in the locked position into a V-shaped recess 11 which according to FIG. 4 is formed on the end face end of a positioning element 12.

For unlocking the actuation element 5 this is rotated in a certain direction with an otherwise rigidly held instrument. An opposite rotation of the actuation element is prevented by the fact that in each case the edges 13 of the recesses 9 abut the end faces 14 of the spring elements 7. In contrast, with the rotation of the actuation element 5 in the certain unlocking rotational direction, the spring element 7 are radially forced outwards by the webs 15 formed by shank wallings remaining between the recesses 9, by which means the spring elements are disengaged from the recesses 9. On further rotation of the actuation element 5 in the unlocking rotational direction the chamfered edge 16 of the guiding lug 10 of the actuation element 5 slides along an edge 17 arranged obliquely to the instrument longitudinal axis and limiting the V-shaped end-face cutout 11 of the positioning element 12. In this way the actuation element 5 is simultaneously additionally displaced distally on rotation.

It is to be noted that for unlocking and removing the actuation element 5 the previously mentioned distal displacement of the actuation element which is co-caused by the rotation is fundamentally necessary since the spring elements 7 and the recesses 9 are only disengaged in this momentary position. Since the axial displacement of the actuation element with respect to the receiver 6 is thus effected automatically and thus a pulling of the actuation element 5 distally is not required, the removal of the actuation element 5 is considerably simplified.

According to FIG. 1 to the receiver 6 there connects a cylindrically formed part 18 which accommodates the positioning element 12 and a tubing connection piece 19 arranged laterally at an angle to the longitudinal axis, and which carries a scaling cap 20 on the proximal side. This part 18 and also the receiver 6 are connected to a cylinder sleeve 21 consisting of plastic, and on its lower side there is arranged a thumb ring 22 for actuating the actuation element 5 which engages on the forceps jaw 4 in the known manner.

Furthermore FIG. 1 shows that between the inner part and the actuation element 5 surrounding this as a tube there is formed an annular cylindrical channel 23 through which a rinsing fluid or likewise may be supplied or removed. Through the tubing connection piece 19 provided at the proximal end of the annular cylindrical channel 23 rinsing fluid may be introduced into the channel 23.

So that no rinsing fluid may exit from the instrument part located outside of the body cavity the proximal end of the channel 23 is closed by a sealing cap 20 in a fluid-tight manner, this cap being placed on an olive handle 24 formed on the part 18.

An annular seal 25 arranged in the receiver 6 prevents additionally a fluid exit between the annular gap remaining between the actuation element 5 and the receiver 6.

We claim:

1. A medical instrument comprising a body having a proximal end and a distal end, an inner part releasably fastened in the body at the proximal end, a distal end of the inner part carrying a tool which can be actuated by way of an actuation element adjustable axially and relative to the inner part and the tool, wherein the actuation element is releasably lockable in a proximal, axially adjustable receiver, the annular received being connected to a positioning element; and a proximal end of the actuation element lying within the annular receiver comprising at least one recess and wherein the receiver comprises at least one spring element which is laterally displaced with respect to the instrument longitudinal axis and which in a locking position resiliently engages into the recess, the spring element cooperating with the recess in the actuation element in a manner such that the actuation element in the receiver is only rotatable in one direction and when the actuation element is rotated in the one direction the spring element comes out of engagement with the recess and, at the same time the positioning element drives the actuation element away from the proximal end of the instrument.

2. A medical instrument according to claim 1, wherein the actuation element is tubular and surrounds the inner part.

3. A medical instrument according to claim 1, wherein the proximal end of the actuation element comprises three recesses displaced about 120 degrees in a circumferential direction and the receiver comprises three spring elements corresponding to the three recesses, which are arranged displaced by 120 degrees to one another and are laterally displaceable with respect to the instrument longitudinal axis.

4. A medical according to claim 1, wherein the proximal end of the actuation element further comprises a guiding lug in the form of a wall section projecting in the axial direction and tapering proximally, the guiding lug engaging into one of a plurality of corresponding V-shaped end-face recesses of the positioning element.

5. A medical instrument according to claim 4, wherein the positioning element comprises three V-shaped recesses displaced about 120 degrees to one another.

6. A medical instrument according to claim 4, wherein the actuation element includes a lateral edge which upon unlocking rotation slides along an edge of the positioning element corresponding to the lateral edge, the edge of the positioning element being arranged obliquely to the instrument axis and defining the V-shaped recess, wherein the sliding of the lateral edge along the edge of the positioning element causes the distal driving of the actuation element.

7. A medical instrument according to claim 4, wherein the receiver and the positioning element are connected to an outer cylinder sleeve which surrounds them and on which there is arranged an actuation member operable by hand for the axial displacement of the actuation element and for actuating the tool.

8. A medical instrument according to claim 1, wherein the actuator element includes a cylindrical inner wall and between the cylindrical inner wall of the actuation element and the inner part there is formed an annular cylindrical rinsing channel for supplying and removing rinsing fluid.

9. A medical instrument according to claim 8, wherein within a cylinder sleeve there is provided a sealing cap for sealing the rinsing channel.

10. A medical instrument according to claim 8, wherein in the region of the positioning element at the proximal end of the annular cylindrical rinsing channel there lies a tubing connection piece via which the rinsing fluid may be introduced into the rinsing channel.

11. A medical instrument, comprising:

a body having a distal end and a proximal end;

an inner part that is releasably fastened in the body and carrying a tool on an end opposite the proximal end of the body;

an actuation element releasably engaged inside a distal end of the body and capable of causing the inner part to manipulate the tool, the actuation element being rotatably adjustable about the inner part and having at least one recess;

an annular receiver positioned in the body proximate the distal end, the annular receiver having at least one spring element which is engageable with the at least one recess in the actuation element, the at least one spring element being disposed so that the actuation element is only rotatable in one direction, a positioning element connected to the annular receiver; and the positioning element driving the actuation element away from the proximal end of the body at the same time that the at least one recess in the actuation element is disengaged from the at least one spring element during rotation in the one direction.

12. A medical instrument, comprising:

a body having a distal end and a proximal end;

an inner part that is releasably fastened in the body and carrying a tool on an end opposite the proximal end of the body;

an actuation element releasably engaged inside a distal end of the body and capable of causing the inner part to manipulate the tool, the actuation element having a tubular shape and surrounding the inner part, the actuation element being rotatably adjustable about the inner part and having at least one recess;

an annular receiver positioned in the body proximate the distal end, the annular receiver having at least one spring element which is engageable with the at least one recess in the actuation element, the at least one spring element being disposed so that the actuation element is only rotatable in one direction, a positioning element connected to the annular receiver; and the positioning element driving the actuation element away from the proximal end of the body at the same time that the at least one recess in the actuation element is disengaged from the at least one spring element during rotation in the one direction.

* * * * *